(12) United States Patent
Pedersen (10) Patent No.: US 11,584,905 B2
(45) Date of Patent: Feb. 21, 2023

(54) APPARATUS FOR THE COMBINED INCUBATION AND VITRIFICATION OF A BIOLOGICAL MATERIAL

(71) Applicant: Esco Medical UAB, Kaunas (LT)

(72) Inventor: Thomas William Pedersen, Skanderborg (DK)

(73) Assignee: Esco Medical Technologies, UAB, Kaunas (LT)

( * ) Notice: Subject to any disclaimer, the term of this patent is extended or adjusted under 35 U.S.C. 154(b) by 593 days.

(21) Appl. No.: 15/466,019

(22) Filed: Mar. 22, 2017

(65) Prior Publication Data

US 2018/0002649 A1    Jan. 4, 2018

(30) Foreign Application Priority Data

Jul. 1, 2016 (DK) .......................... PA 2016 00392

(51) Int. Cl.
| | | |
|---|---|---|
| *C12M 3/00* | (2006.01) | |
| *C12M 1/32* | (2006.01) | |
| *C12M 1/26* | (2006.01) | |
| *C12M 1/00* | (2006.01) | |
| *C12M 1/34* | (2006.01) | |
| *C12M 1/36* | (2006.01) | |
| *A01N 1/02* | (2006.01) | |

(52) U.S. Cl.
CPC .......... *C12M 21/06* (2013.01); *A01N 1/0221* (2013.01); *A01N 1/0242* (2013.01); *A01N 1/0257* (2013.01); *C12M 23/12* (2013.01); *C12M 23/50* (2013.01); *C12M 33/04* (2013.01); *C12M 41/14* (2013.01); *C12M 41/34* (2013.01); *C12M 41/36* (2013.01); *C12M 41/46* (2013.01); *C12M 41/48* (2013.01); *C12M 47/20* (2013.01)

(58) Field of Classification Search
CPC ................ A01N 1/0221; A01N 1/0242; A01N 1/0257; A01N 1/02; B60K 7/00; C12M 21/06; C12M 23/12; C12M 23/50; C12M 33/04; C12M 41/14; C12M 41/34; C12M 41/36; C12M 41/46; C12M 41/48; C12M 47/20; C12M 1/00; C12M 1/26; C12M 1/32; C12M 1/34; C12M 1/36; C12M 3/00; G21F 5/14; G21F 9/34

See application file for complete search history.

(56) References Cited

U.S. PATENT DOCUMENTS

2018/0072980 A1 * 3/2018 Koike ............... C12M 1/00
2018/0087021 A1 * 3/2018 Blanchard ........ C12M 41/14
2018/0346868 A1 * 12/2018 Blanchard ........ C12M 23/50

FOREIGN PATENT DOCUMENTS

WO    WO 2014/106286    7/2014

* cited by examiner

*Primary Examiner* — Lydia Edwards
(74) *Attorney, Agent, or Firm* — Leason Ellis LLP (57) ABSTRACT

An apparatus, that relates to the field of in vitro fertilization, is provided for the combined incubation and vitrification of a biological material. The apparatus can be configured to allow for automatic incubation and vitrification of a viable biological material. Thereby predetermined protocols for handling the biological material can be performed precisely and accurately thus avoiding errors and deviations from the intended protocol, as caused by manual human intervention.

19 Claims, 8 Drawing Sheets

APPARATUS FOR THE COMBINED INCUBATION AND VITRIFICATION OF A BIOLOGICAL MATERIAL

CROSS-REFERENCE TO RELATED PATENT APPLICATIONS

This application is based on and claims priority to Danish Patent Application No. PA 2016 00392, filed Jul. 1, 2016, the entire contents of which is incorporated by reference herein as if expressly set forth in its respective entirety herein.

FIELD OF THE INVENTION

The present invention relates to the field of in vitro fertilization. More specifically the present invention relates in a first aspect to an apparatus for the combined incubation and vitrification of a viable biological material. In a second aspect the present invention relates to a system for the combined incubation and vitrification of a viable biological material. In a third aspect the present invention relates to a culture dish for use with the apparatus according to the first aspect of the present invention. In a fourth aspect the present invention relates to the use of the apparatus, or of the system, or of the culture dish according to the first, second and third aspect, respectively, for incubation and vitrification of a viable biological material.

BACKGROUND OF THE INVENTION

The development of in vitro fertilization (IVF) has for the last few decades resulted in considerably improved methods and techniques thus leading to improved success rates in terms of enhanced birth rates relating to successful births originating from such techniques.

In vitro fertilization involves capturing a ripened egg from a female ovary, fertilizing the ovary with a spermatozoon, incubating the fertilized egg under a controlled environment and subsequently inserting the fertilized and incubated egg in the female's uterus.

As in vitro fertilization is most commonly used by females or couples which notoriously are having problems in getting pregnant the natural way, thus implying some degree of reduced fertility by the male or female counterpart of the couple, or both, and as in vitro fertilization techniques involves quite expensive procedures these in vitro fertilization techniques are usually performed in a way that seek to optimize efficiency, especially in view of the fact that frequently more than one insertion of a fertilized egg into the female' uterus will be necessary in order to encounter a successful pregnancy.

Accordingly, in order to make the in vitro fertilization techniques efficient, the female is typically provided with a hormone treatment prior to harvesting an egg from her ovary.

Such hormone treatment will make the female ovary ovulate not only one egg, but a multitude of eggs at the same time.

These eggs are then either fertilized and incubated immediately, or alternatively they are preserved at cryogenic conditions with the view to be used in an in vitro fertilization at a later stage. Due to the hormone treatment, a certain amount of time has to lapse however, before the female body is ready to receive the fertilized egg.

Techniques involving cryogenic preservation of an egg per se, as well as a fertilized egg have been developed.

In the cryogenic preservation of a biological sample, such as an egg or a fertilized egg one faces the challenges of avoiding mechanical damages to the biological samples due to formation of crystals within the biological sample, which formation of crystals may physically destroys the organelles responsible for the metabolism within the biological sample.

In order to avoid such formation of crystals within a biological sample, a technique called vitrification has been invented. Vitrification accordingly involves preparing a viable biological material in such a way that it may be freezed in a way where formation of crystals upon freezing is not taking place, or at least takes place to a limited extension.

Vitrification may involve treating the biological sample with one or more "vitrification liquids", also denoted "cryoprotectants". Osmosis may be involved so that water is being drained from the biological sample prior to the freezing step.

Apparatuses for vitrification of fertilized an unfertilized eggs have been developed. WO 2014/106286 A1 discloses an apparatus and a method for vitrification of a biological sample, such as an oocyte or an embryo. The apparatus comprises a compartment for accommodating a tray comprising one or more separated biological samples. The tray comprises a number of pods each comprising a biological sample. The tray also comprises a number of vials each comprising a vitrification liquid. Automation means provides for automated movement of pipettes with the view to prepare the biological samples for cryogenic storage by adding and removing vitrification liquids to and from the pods containing the vitrification liquid.

The addition and removing of vitrification liquids to and from the biological samples is performed according to predetermined procedures and protocols.

After the subjection the biological sample to the various vitrification liquids, the pod containing the biological sample is automatically sealed by automatically arranging a lid onto the pod, thus sealing off the biological sample from the surroundings. Subsequently, the pod containing one or more separated biological samples are manually submerged in liquid nitrogen contained in a vessel which is an integral, yet separable item of the apparatus.

The apparatus disclosed in WO 2014/106286 A1 does not comprise electronic image capturing means for monitoring the biological material. Furthermore, the apparatus disclosed in WO 2014/106286 A1 is not suitable for monitoring and controlling the development of a viable biological material during the incubation per se thereof.

As indicated in the previous sections both oozytes and fertilized eggs, e.g. embryos may be subjected to vitrification. In case of fertilized eggs, before vitrification of a zygote the egg is fertilized. Such fertilization and subsequent incubation of the resulting zygote is being performed in an incubator. On the marked a number of different incubators are available. Some of these allow for controlling the environment of the incubated biological material, such as controlling the temperature and the composition of the air surrounding the biological material. Other types of incubators include image capturing means for monitoring the biological material. Some of these comprise time lapse techniques allowing monitoring of the biological material in order to determine a cell division stage which will be optimum in relation to finding the right time to insert the fertilized egg into the uterus of a female.

However, none of these incubators include means for performing a vitrification of the biological material.

None of the prior art apparatuses for vitrification of a biological material provides for a fully automatic vitrification process, including a fully automatic preparational step and/or a subsequent cryogenic processing of the biological material.

Thirdly, none of the prior art apparatuses for vitrification of a biological material provides for image capturing of the vitrification process.

BRIEF DESCRIPTION OF THE INVENTION

It is the objective of the present invention to provide apparatuses and uses which overcome these disadvantages.

This objective is fulfilled with the present invention in its various aspects.

Accordingly, the present invention relates in a first aspect to an apparatus 100 for the combined incubation and vitrification of a viable biological material;
said apparatus comprises:
a housing having an extension in a longitudinal direction and an extension in a transversal direction; said housing comprising:
one or more culture dish compartments, each being adapted to accommodate one or more culture dishes comprising a biological material, each said culture dish comprises one or more culture wells for accommodating said biological material;
wherein said apparatus comprises one or more image capturing devices adapted to capture images of one or more of said biological material accommodated in said one or more culture dishes;
wherein said apparatus comprises cryogenic means for cooling at cryogenic temperatures of a biological material, said cryogenic means being arranged in a cryogenic area at a different location relative to said one or more culture dish compartments;
wherein said one or more culture dish compartments and said cryogenic area together defines an operational area;
wherein said apparatus comprises one or more manipulation units, said one or more manipulation units each comprises one or more robotic arms, said one or more robotic arms being configured to grip and move elements and/or chemical/biological material within said operational area;
wherein said apparatus comprises movement means, said movement means being configured to move said image capturing device relative to said culture dishes;
wherein said apparatus comprises a control system for controlling the operation thereof, wherein said control system being configured to allow a user to input predetermined operation protocol(s) to be followed by said apparatus; and wherein said control system being configured to control said apparatus according to said protocol(s).

In a second aspect the present invention relates to a system for the combined incubation and vitrification of a viable biological material; said system comprises:
an apparatus according to the first aspect of the present invention in combination with
one or more culture dishes.

In a third aspect the present invention relates to a culture disc as defined in respect of the second aspect.

In a fourth aspect the present invention relates to the use of an apparatus according to the first aspect of the present invention, or of a system according to the second aspect of the present invention; or of a culture dish according to the third aspect of the present invention for incubation and vitrification of a viable biological material.

In a fifth aspect the present invention relates to a method for the combined incubation and vitrification of a viable biological material, wherein said method is being performed by using an apparatus according to the first aspect of the present invention.

The present invention in its various aspects provide for improved processing quality upon performing a combined incubation and vitrification of a viable biological material.

As the apparatus according to the present invention may be controlled fully automatically, thereby minimizing procedure variations caused by human handling and/or human interaction it is possible to use the apparatus of the invention for research purposes with the view to find optimized conditions for incubation and for vitrification of a viable biological sample, such as an embryo or an oocyte, for example a human embryo or a human oocyte.

Such optimized conditions for incubation and for vitrification may be found with the apparatus according to the present invention by running a huge number of experiments of incubations and vitrifications, in which one experiment varies from another experiment by only one parameter.

As indicated above precise experiments may be performed as the apparatus of the invention allows for minimizing unintended fluctuations in experimental conditions caused by human intervention as the apparatus may be controlled fully automatic thereby ensuring constant operational protocols from experiment to experiment.

In this way each parameter may be optimized and eventually a complete set of optimizes parameters for incubation and vitrification of a viable biological material may be obtained.

Once this this is established, the apparatus according to the present invention may also be used commercially for commercial incubation and vitrification of a viable biological material, such as for example a human embryos or a human oocytes.

DETAILED DESCRIPTION OF THE INVENTION

The present invention relates in a the present invention relates in a first aspect to an apparatus for the combined incubation and vitrification of a viable biological material; said apparatus comprises:

a housing having an extension in a longitudinal direction and an extension in a transversal direction; said housing comprising:

one or more culture dish compartments, each being adapted to accommodate one or more culture dishes comprising a biological material, each said culture dish comprises one or more culture wells for accommodating said biological material;

wherein said apparatus comprises one or more image capturing devices adapted to capture images of one or more of said biological material accommodated in said one or more culture dishes;

wherein said apparatus comprises cryogenic means for cooling at cryogenic temperatures of a biological material, said cryogenic means being arranged in a cryogenic area at a different location relative to said one or more culture dish compartments;

wherein said one or more culture dish compartments and said cryogenic area together defines an operational area;

wherein said apparatus comprises one or more manipulation units, said one or more manipulation units each comprises one or more robotic arms, said one or more robotic arms being configured to grip and move elements and/or chemical/biological material within said operational area;

wherein said apparatus comprises movement means, said movement means being configured to move said image capturing device relative to said culture dishes;

wherein said apparatus comprises a control system for controlling the operation thereof, wherein said control system being configured to allow a user to input predetermined operation protocol(s) to be followed by said apparatus; and wherein said control system being configured to control said apparatus according to said protocol(s).

The apparatus according to the first aspect of the present invention allows for automatic incubation and vitrification of a viable biological material. Thereby predetermined protocols for handling the biological material can be performed precisely and accurately thus avoiding errors and deviations from the intended protocol, as caused by manual human intervention.

In one embodiment of the apparatus according to the first aspect of the present invention the apparatus comprises one or more individual culture dish compartments; such as 2-25, for example 3-24, such as 4-23, e.g. 5-22, such as 6-21, e.g. 7-20 or 8-19, for example 9-18, such as 10-17, for example 11-16, such as 12-15 or 13-14 individual culture dish compartments.

Such numbers of separate culture dish compartments allows in a research situation to conduct a number of parallel protocols wherein each protocol differs by only one parameter from one culture dish compartment to another. Thereby optimization of protocols for the combined incubation and vitrification of a specific type of viable biological material may be determined.

In one embodiment of the apparatus according to the first aspect of the present invention one or more of said individual culture dish compartments, preferable all said individual culture dish compartments comprises an individual compartment lid.

By providing individual and separate culture dish compartments with its own individual lid, it is assured that the environment of one culture dish compartment may be kept at predetermined conditions independent of the environment of the other culture dish compartments.

In one embodiment of the apparatus according to the first aspect of the present invention the apparatus furthermore comprising temperature regulating means for individual regulating the temperature in one or more of said individual said culture dish compartments, preferable in all said individual said culture dish compartments.

By providing individual and separate culture dish compartments with its own individual temperature regulating means for individual regulating the temperature, it is assured that the environment of one culture dish compartment may be kept at predetermined conditions independent of the environment of the other culture dish compartments.

In one embodiment of the apparatus according to the first aspect of the present invention the temperature regulating means comprising heating means, such as one or more electric heating elements; and/or cooling means, such as one or more Peltier elements.

In one embodiment of the apparatus according to the first aspect of the present invention the apparatus furthermore comprising gas composition regulating means for individual regulating the gas composition, such as the concentration of oxygen, carbon dioxide and/or nitrogen in one or more of said individual said culture dish compartments, preferable in all said individual said culture dish compartments.

By providing individual and separate culture dish compartments with its own individual gas composition regulating means for individual regulating the gas composition, it is assured that the environment of one culture dish compartment may be kept at predetermined conditions independent of the environment of the other culture dish compartments.

In one embodiment of the apparatus according to the first aspect of the present invention apparatus comprises an image capturing device in respect of each individual culture dish compartment.

Providing each individual culture dish compartment with an image capturing device assures the ability of capturing images of each culture well in each culture dish being accommodated in each individual culture dish compartment.

In one embodiment of the apparatus according to the first aspect of the present invention said movement means are configured in such a way that said image capturing device is adapted for being moveable relative to said culture dish, thereby allowing capturing of images of each biological material accommodated in said culture dish(es).

Allowing one image capturing device to be responsible for capturing images relating to biological material being accommodated in different culture dish compartments saves production cost in the manufacture of the apparatus.

In one embodiment of the apparatus according to the first aspect of the present invention and in respect of one or more culture dish compartments, preferably all culture dish compartments, said culture dish compartment comprises a shelf for accommodation of a culture dish, wherein said movement means are configured in a way allowing said shelf to be moved, preferably by rotation, relative to said image capturing device, thereby allowing capturing of images of each biological material accommodated in said culture dish(es).

In this way, a single image capturing device may capture images relating to biological material being accommodated in different culture dish compartments.

In one embodiment of the apparatus according to the first aspect of the present invention, for example in respect of one or more culture dish compartments, preferably all culture dish compartments, said culture dish compartment comprises a pipette pump, said pipette pump being configured for pipetting fluids to and from culture well(s) of said culture dish(es).

The pipette pump allows adding and removing from one or more culture wells of the culture dishes of culture media and cryoprotectants.

In one embodiment of the apparatus according to the first aspect of the present invention and in respect of one or more culture dish compartments, preferably all culture dish compartments, said culture dish compartment comprises one or more pipette stands comprising one or more pipettes.

A pipette stand may act as a holder for used and/or unused pipettes, thus allowing exchange of pipettes during the operation of the apparatus with the view to avoid any contaminations of the viable biological material.

In one embodiment of the apparatus according to the first aspect of the present invention, and in respect of one or more culture dish compartments, preferably all culture dish compartments, said culture dish compartment comprises one more containers for storing incubation liquids and/or cryoprotectants.

Providing the culture dish compartments with such containers allows for easy access to such incubation liquids and/or cryoprotectants.

In one embodiment of the apparatus according to the first aspect of the present invention each said one or more containers comprising a sealing syringe end cap.

A sealed syringe end cap minimizes the risk of contamination of such incubation liquids and/or cryoprotectants, while still allowing a pipette to access the interior of such containers.

In one embodiment of the apparatus according to the first aspect of the present invention and in respect of one or more of said individual culture dish compartments, preferably in respect of each individual culture dish compartment, said individual culture dish compartment comprises a transparent shelf for carrying a culture dish; and wherein said image capturing device is arranged below said shelf and being adapted to be movable so as to enable capturing images, through said shelf, of biological material accommodated in said culture dishes.

In one embodiment of the apparatus according to the first aspect of the present invention and in respect of one or more of said individual culture dish compartments, preferably in respect of each individual culture dish compartment, said individual culture dish comprises one or more transparent walls.

In such an embodiment said image capturing device may be configured for focusing in a horizontal direction or in an essentially horizontal direction.

In one embodiment of this embodiment said image capturing device is being configured for being movable along said one or more individual culture dish compartments at positions outside said transparent wall(s), relative to the interior of said individual culture dish compartments.

Such movement of the image capturing device may be in front of said one or more culture dish compartments, or behind said one or more culture dish compartments, while still being present within the housing of the apparatus.

These embodiments of having one or more culture dish compartments provided with transparent walls and having said image capturing device may be configured for focusing in a horizontal direction or in an essentially horizontal direction allows use of an alternative type of culture dishes. Such culture dishes may be in the form of a flat element having a top surface wherein one or more culture wells are being arranged at said top surface; and wherein these types of culture dishes are being configured to be arranged, during incubation and/or vitrification, in an upright or vertical orientation.

These various set-ups allow for easy capturing of images by the image capturing device in respect of one or more culture dish compartments.

In one embodiment of the apparatus according to the first aspect of the present invention, and in respect of one or more of said individual culture dish compartments, preferably in respect of each individual culture dish compartment, said individual culture dish compartment comprises one or more of the following: a pH sensor, a temperature sensor, an oxygen sensor, a carbon dioxide sensor.

Such sensors allows for monitoring the environment in the particular culture dish compartment.

In one embodiment of the apparatus according to the first aspect of the present invention said cryogenic means comprising a container for storing a liquid gas, such as liquid nitrogen; said container for storing of a liquid gas is separated from said one or more culture dish compartments.

Liquid gas, such as liquid nitrogen, is a readily available and cost efficient and in terms of cryogenic power represents an efficient cryogenic mean.

In the present description and in the appended claims, however, the term "cryogenic mean" shall be understood to mean a container per se for storing a liquid gas.

In one embodiment of the apparatus according to the first aspect of the present invention said apparatus comprises input means for allowing a user to program and select one or more operation protocols to be followed by said apparatus.

In one embodiment of the apparatus according to the first aspect of the present invention said apparatus comprises a display for displaying to an operator the status and/or progression of the operation of the apparatus.

Such input means and display allows an operator to control and monitor the operation of the apparatus.

In one embodiment of the apparatus according to the first aspect of the present invention said apparatus comprising an image processing unit for processing images captured by said image capturing device.

In one embodiment of the apparatus according to the first aspect of the present invention said image processing unit being configured to provide, from the images captured by said image capturing device, time-lapse image series of one or more of the individual biological materials.

In one embodiment of the apparatus according to the first aspect of the present invention said image capturing device comprises a microscope for capturing close-up images of said biological material.

Time lapse imaging allows one to monitor the development of a particular viable biological material with the view to assess the quality of such a material with the view to selecting a particular biological material for further processing steps.

In one embodiment of the apparatus according to the first aspect of the present invention, and in respect of one or more of said individual culture dish compartments, preferably in respect of each individual culture dish compartment, said individual culture dish compartment comprises lid holding means for accommodating one or more lids for said culture dish or for individual culture wells of said culture dish.

Providing the culture dish compartments with such lids allows for easy access to such lids with the view to seal individual culture dishes and/or individual culture wells of individual culture dishes prior to the cryogenic process.

In one embodiment of the apparatus according to the first aspect of the present invention one of said one or more manipulation units comprises a robotic dish sealing arm, wherein said robotic dish sealing arm is being configured for sealing one or more culture dishes, or for sealing a well of a culture dish, being accommodated within said culture dish compartment.

In one embodiment of the apparatus according to the first aspect of the present invention said robotic dish sealing arm being in the form of a robotic lid mounting arm configured to grip a lid from within said culture dish compartment and to move said lid and arrange said lid on top of a culture dish or of a well of a culture dish being accommodated within said culture dish compartment.

Thereby the apparatus may be configured for automatic sealing a culture dish or one or more wells of a culture disc according to a predetermined protocol. Sealing of the culture dish, or of the individual culture wells of the culture dish will be necessary prior to the cryogenic step to be performed.

In the present description and in the appended claims the term "robotic dish sealing arm" shall however be interpreted to mean a robotic arm which is configured for providing movements which will result in sealing off one or more culture wells of a culture dish, from the surroundings.

In one embodiment of the apparatus according to the first aspect of the present invention one of said one or more manipulation units comprises a robotic pipetting arm, said robotic pipetting arm comprises a pipette and wherein said robotic pipetting arm being configured to move said pipette within said culture dish compartment, so as to allow withdrawing and/or adding liquids and/or suspensions to and/or from one or more culture wells of a culture dish being accommodated within said culture dish compartment.

Thereby the apparatus may be configured for automatic exchange of incubation liquids and/or cryoprotectants in one or more wells of a culture disc according to a predetermined protocol.

In one embodiment of the apparatus according to the first aspect of the present invention one of said one or more manipulation units comprises a robotic culture dish moving arm, wherein said robotic culture dish moving arm being configured to grip a culture dish and to move it between said culture dish compartment and said cryogenic area of said apparatus.

Thereby the apparatus may be configured for automatic movement of the culture dish from a particular culture dish compartment to the cryogenic area with the view to subject that culture dish to cryogenic conditions.

The robotic culture dish moving arm and the robotic dish sealing arm, e.g. in the form of a robotic lid mounting arm, may be combined into one and the same arm.

In one embodiment of the apparatus according to the first aspect of the present invention one or more of said robotic arms independently comprises a base and wherein said robotic arm being pivotally mounted on said base in said culture dish compartment and wherein the robotic arm in the opposite end thereof comprises a working end, said working end of said robotic arm being able to be moved independently in three dimensions.

Hereby flexibility in movement of the robotic arms is ensured.

In one embodiment of the apparatus according to the first aspect of the present invention said control system for controlling the operation of said apparatus is configured to control one or more of the following: said temperature regulating means in respect of one or more of the culture dish compartments; said gas composition regulating means in respect of one or more of the culture dish compartments; said one or more of said image capturing devices; said one or more manipulation units, such as a said one or more robotic lid mounting arms, said one or more robotic pipetting arms, said one or more robotic culture dish moving arm; and/or said one or more pipette pumps.

Such control system allows for a fully automatic control of said apparatus according to predetermined protocols. This will avoid fluctuations in intended protocols caused by manual human interference and human error.

In a second aspect the present invention relates to a system for the combined incubation and vitrification of a viable biological material; said system comprises:
an apparatus according to the first aspect of the present invention in combination with
one or more culture dishes.

In one embodiment of the system according to the second aspect of the present invention said one or more culture dishes comprises a material comprising a number of culture wells, each representing a cavity in said material.

In one embodiment of the system according to the second aspect of the present invention the number of culture wells in each culture dish is 2-20, such as 4-18, for example 6-16, such as 8-14, for example 10-12.

Such numbers of culture wells allows in a research situation to conduct a number of parallel protocols wherein each protocol differs by only one parameter from one culture well to another. Thereby optimization of protocols for the combined incubation and vitrification of a specific type of viable biological material may be determined.

In one embodiment of the system according to the second aspect of the present invention at least in respect of one or more of said the culture wells, the material of the dish below each well is being transparent.

In one embodiment of the system according to the second aspect of the present invention the material of the culture dish is a polymer such as a plastic.

Providing material of the dish below each well is with transparency allows an image capturing device to be arranged below said culture dish and still be able to capture images of a biological material being accommodated in wells of said culture dish.

In one embodiment of the system according to the second aspect of the present invention and in respect of one or more of said the culture wells, the area surrounding said well is provided with a material having relative high heat conduction capacity, such as a metal.

In one embodiment of the system according to the second aspect of the present invention each culture well is arranged in close vicinity to a periphery of said dish; and wherein said dish at its bottom surface is covered with a material having relative high heat conduction capacity, such as a metal; and wherein the area of the culture wells, at a bottom surface thereof is not covered by said material having relative high heat conduction capacity.

In one embodiment of the system according to the second aspect of the present invention the culture dish comprises an essentially central oriented through-going hole, thereby having an outer periphery and an inner periphery; and wherein each culture well is arranged in close vicinity to said inner or outer periphery.

In one embodiment of the system according to the second aspect of the present invention said culture dish comprises a material having a thickness in respect of locations in vicinity to one or more of said culture wells, such as in respect of the material below one or more of said culture wells and/or in respect of the wall of said well of 0.05-0.5 mm, such as 0.06-0.4 mm, for example 0.07-0.3 mm, e.g. 0.08-0.2 mm, for example 0.09-0.1 mm.

These latter four embodiments allows for rapid cooling of the viable biological material by the cryogenic means, thereby obtaining optimum cryogenic conditions.

In one embodiment of the system according to the second aspect of the present invention said culture dish comprises a lid covering all culture wells; or comprising individual lids, each lid covering a single culture well, wherein said lid(s) is/are configured for detachable sealing off said culture wells from the surroundings.

In a third aspect the present invention relates to a culture disc as defined in respect of the second aspect.

In a fourth aspect the present invention relates to the use of an apparatus according to the first aspect of the present invention, or of a system according to the second aspect of the present invention: or of a culture dish according to the third aspect of the present invention for incubation and vitrification of a viable biological material.

In one embodiment of the use according to the fourth aspect of the present invention the biological material being an oocyte or an embryo.

In a fifth aspect the present invention relates to a method for the combined incubation and vitrification of a viable biological material, wherein said method is being performed by using an apparatus according to the first aspect of the present invention.

Although the apparatus according to the first aspect of the present invention has been described as suitable for the combined incubation and vitrification of a biological material, such as a viable biological material, this apparatus may obviously also be used for solely incubation of a biological material.

Likewise, the apparatus of the first aspect of the invention may also be used for solely vitrification of a biological material.

Figure 1:
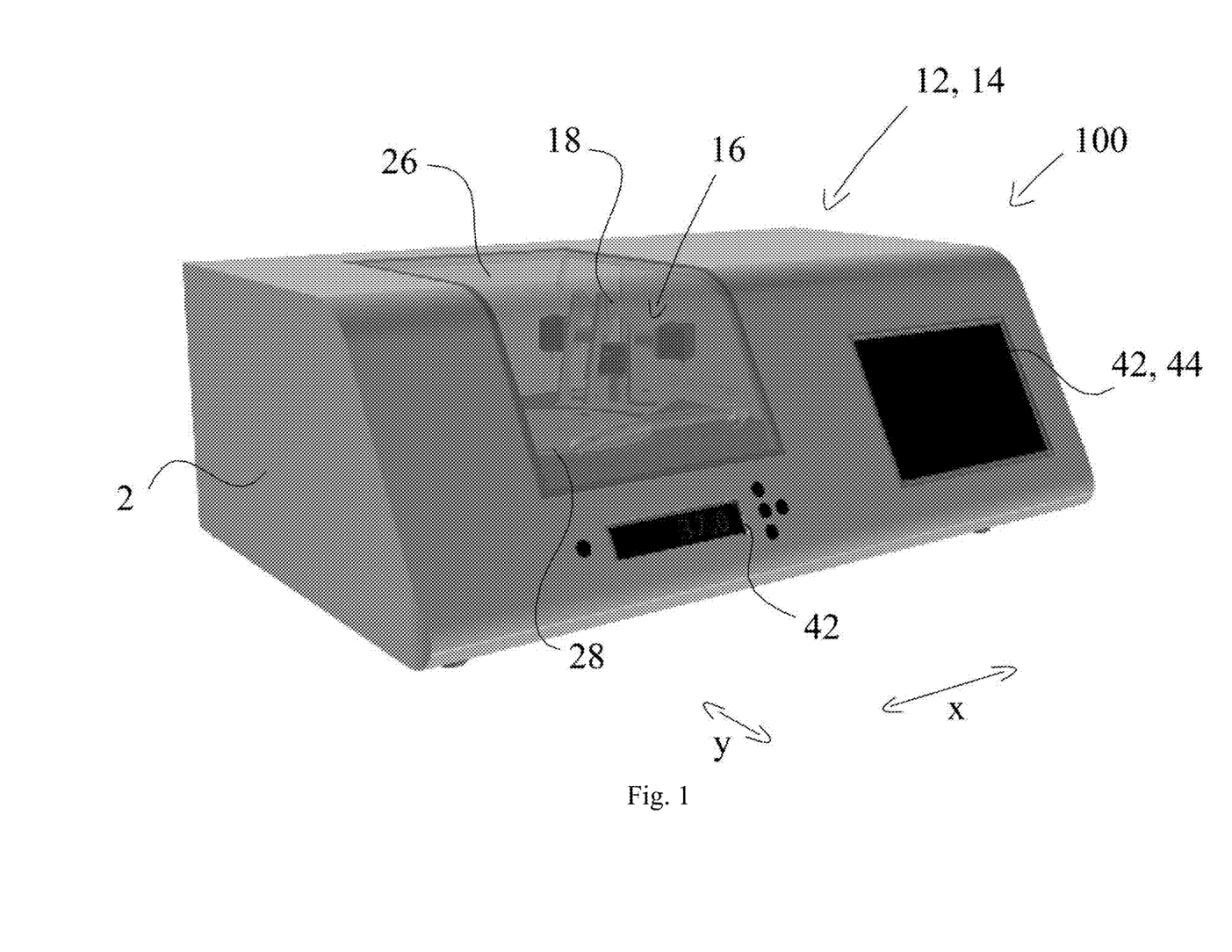
FIG. 1 is a perspective view of the apparatus according to the present invention.

Referring now to the drawings for illustration of the present invention, FIG. 1 shows an apparatus 100 for the combined incubation and vitrification of a viable biological material;

The apparatus of FIG. 1 comprises:

a housing 2 having an extension in a longitudinal direction X and an extension in a transversal direction Y; said housing comprising:

one culture dish compartment 4, being adapted to accommodate a culture dishes 6 comprising biological material, each said culture dish comprises one or more culture wells 8 for accommodating said biological material.

The apparatus comprises an image capturing device 10 (not seen in FIG. 1) adapted to capture images of one or more of said biological material accommodated in the culture dish.

The apparatus furthermore comprises cryogenic means 12 in the form of a container for liquid nitrogen. The container is in FIG. 1 hidden within the housing 2.

The culture dish compartment and said cryogenic area together defines an operational area 16.

The apparatus furthermore comprises a number of manipulation units 18. The manipulation units comprises one or more gripping arms 20, said one or more gripping arms being configured to grip and move elements and/or chemical/biological within said operational area. This is explained further in a subsequent section.

The apparatus comprises movement means 22, said movement means being configured to move said culture dish relative to said image capturing device.

The apparatus comprises a control system 24 for controlling the operation thereof, wherein said control system being configured to allow a user to input predetermined operation protocol(s) to be followed by said apparatus; and wherein said control system being configured to control said apparatus according to said protocol(s).

Figure 2:
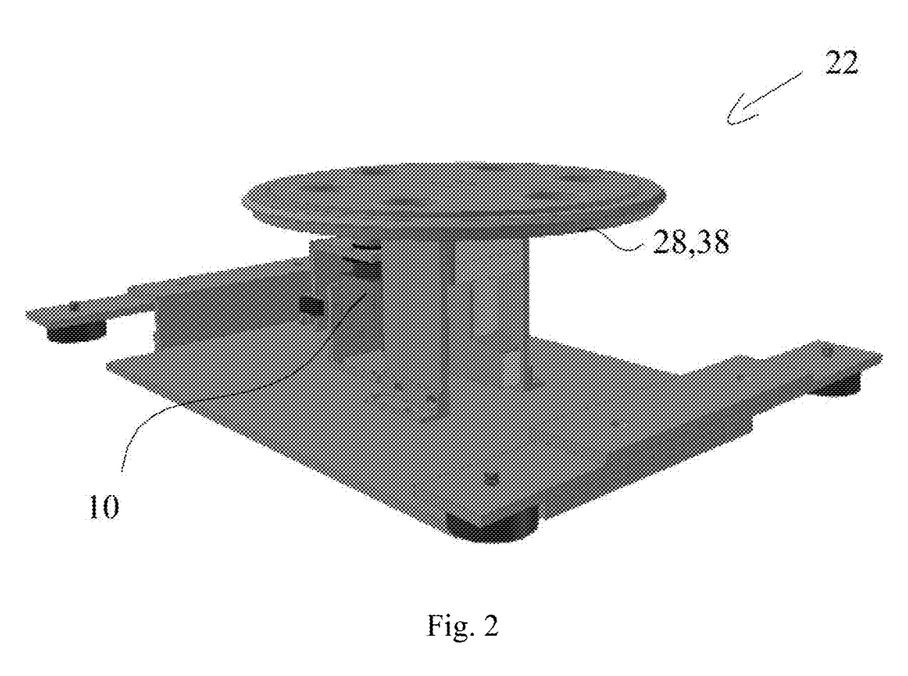
FIG. 2 illustrates in a perspective view one embodiment of a movement means to be used with the apparatus of the present invention.

FIG. 2 illustrates one embodiment of a movement means to be used with the apparatus of the present invention. FIG. 2 shows the image capturing means 10 being arranged below a shelf 28, 38. The movement means is adapted to be moveable relative to the image capturing device 10. In this embodiment, the shelf 28, 38 is designed as a carrousel onto which a culture dish may be arranged. Motor means (not shown in FIG. 2) provides for rotating the shelf 28,28 thereby allowing capturing images of different biological material being accommodated in a different culture wells of a culture dish.

Figure 3:
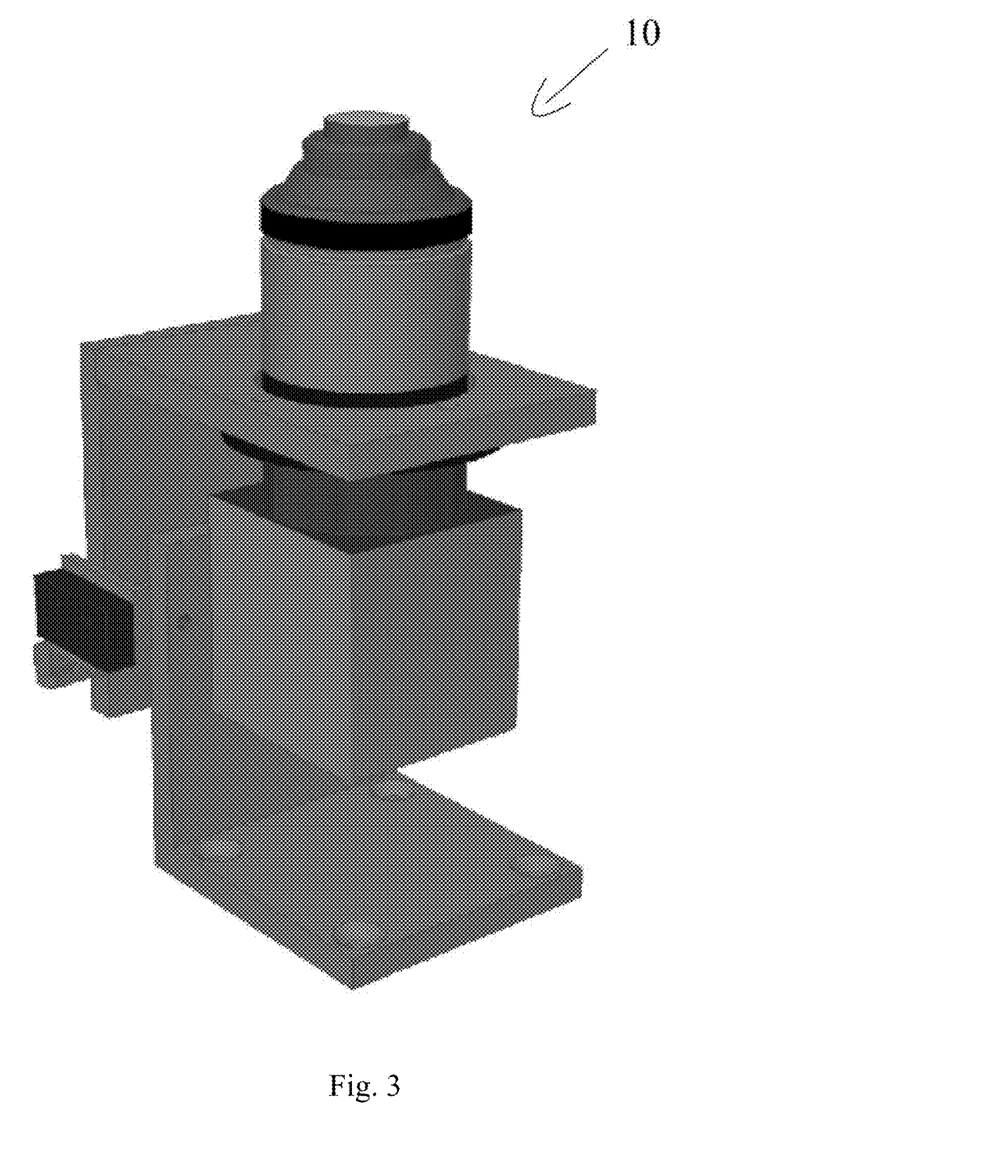
FIG. 3 illustrates in a perspective view a close up of the image capturing device to be used with the apparatus of the present invention.

FIG. 3 illustrates a close up of the image capturing device 10 itself. The image capturing device preferable comprises motorized focusing and/or zooming means. Such means allow for remote and/or automatically adjustment of optical parameters during the process of capturing images.

Figure 4:
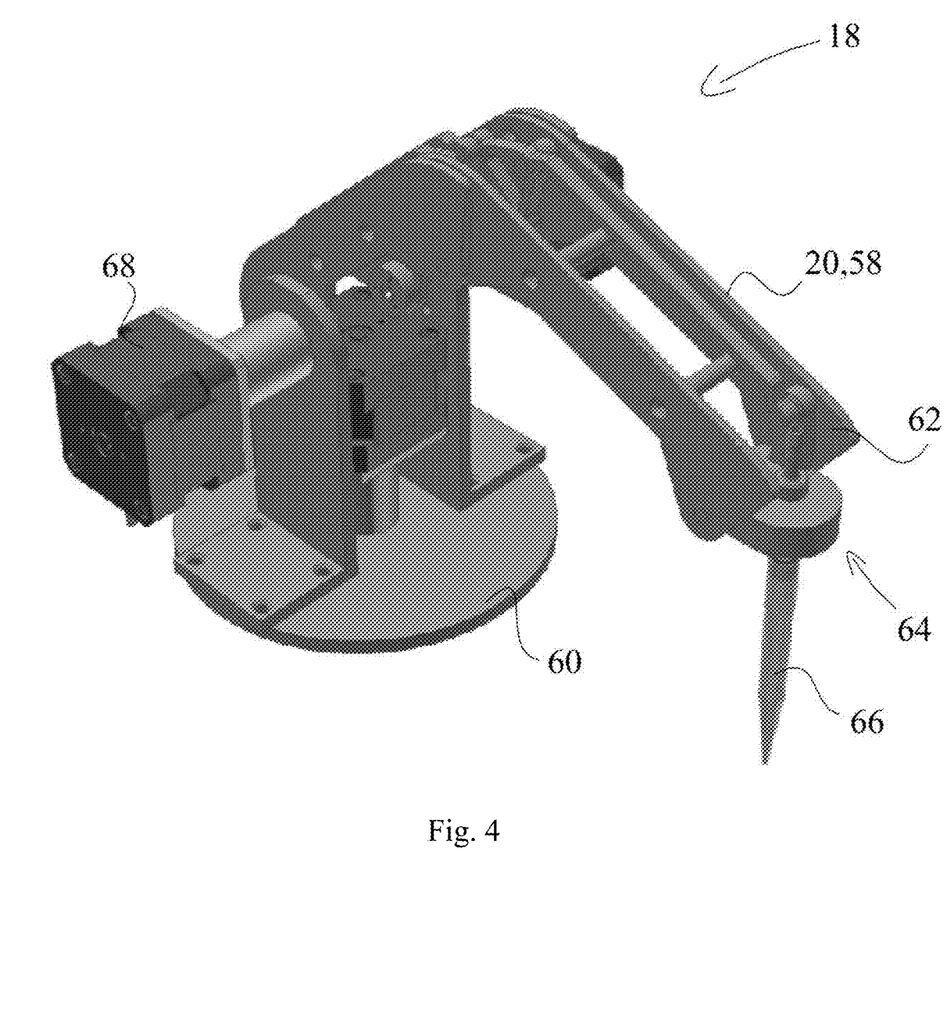
FIG. 4 illustrates in a perspective view one embodiment of a manipulation unit in the form of a robotic pipetting arm to be used with the apparatus of the present invention.

FIG. 4 illustrates one embodiment of a manipulation unit 18. The manipulation unit is in the form of a robotic pipetting arm 58. The robotic pipetting arm is arm being configured to move said pipette within said culture dish compartment, so as to allow withdrawing and/or adding liquids and/or suspensions to and from one or more culture wells of a culture dish being accommodated within said culture dish compartment. This is brought about by pivotally arranging the pipetting arm on a base 60 at one end and at the opposite end providing a working end 62 which by means of a motor unit 68 is being able to be moved independently in three dimensions. The working end comprises pipetting means 64 which in turn comprises a pipette 66. The pipetting means 64 operates as a holder for the pipette 66.

Figure 5:
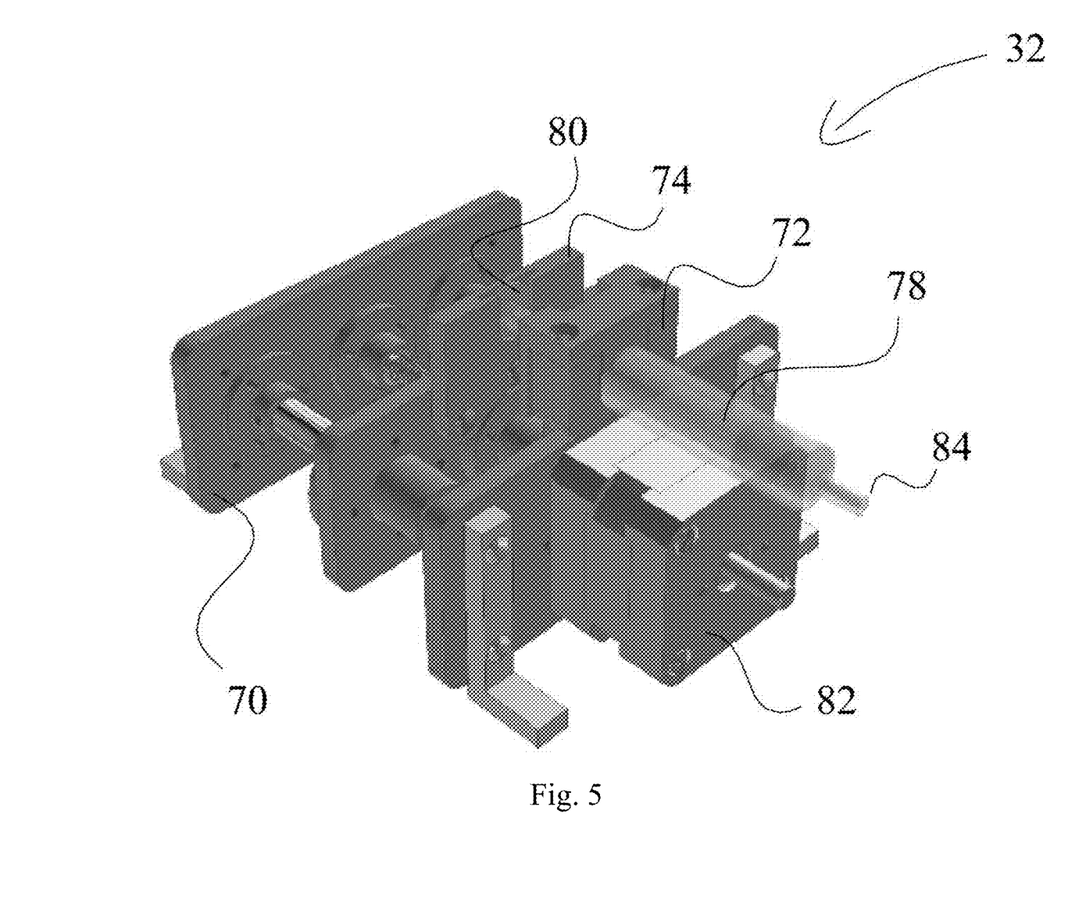
FIG. 5 illustrates in a perspective view one embodiment of a pipette pump to be used with the present invention.

FIG. 5 illustrates one embodiment of a pipette pump 32 to be used with the present invention. The pipette pump 32 comprises a stand 70 comprising a first bracket 72 and a second bracket 74. The first bracket and the second bracket are designed for accommodating a standard disposable plastic syringe 76 having a cylinder part 78 and a piston part 80, in such a way that the first bracket 72 grips around the cylinder part 78 of the syringe and in such a way that the second bracket 74 grips the free end of the piston part 80 of the syringe. A motor unit 82 is configured for moving the first bracket 72 relative to the second bracket 74, thereby making the syringe suck or eject liquids. The passage end 84 of the syringe may be connected to a hose which may be lead to the pipette 66 of the pipetting unit 18 as illustrated in FIG. 4.

Thereby the pipette pump 32 in combination with a pipetting unit 18 as illustrated in FIG. 4 may serve the purpose of adding and removing culture media and/or cryoprotectants to and from culture wells of a culture dish being accommodated in a culture dish compartment of the apparatus 100 of the present invention.

Generally in respect of the apparatus according to the invention, the pipette pump may be shared amongst all culture dish compartments. Alternatively, one or more culture dish compartment may be associated with its own individual pipette pump.

Figure 6:
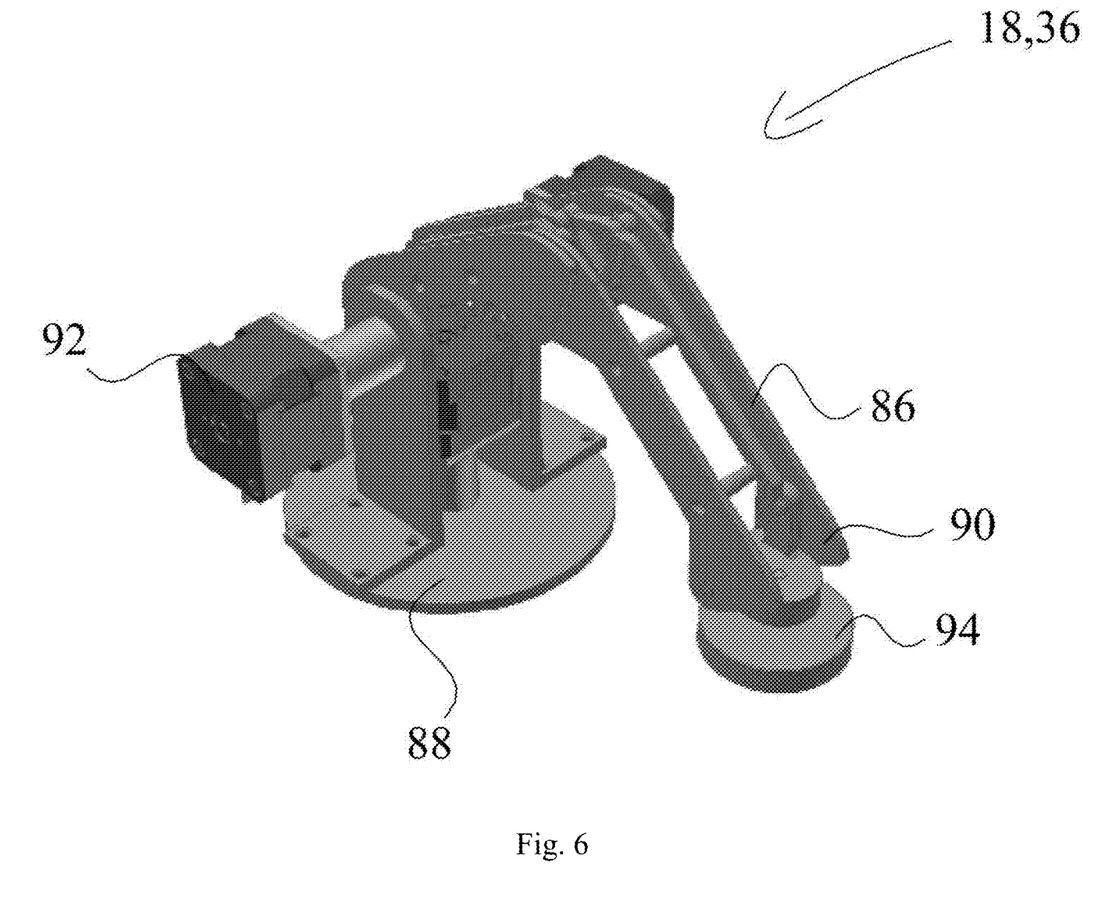
FIG. 6 illustrates in a perspective view one embodiment a manipulation unit in the form of a robotic dish sealing arm to be used with the present invention.

In FIG. 6 is illustrated a manipulation unit 18 in the form of a robotic dish sealing arm 86. The robotic dish sealing arm is in the form of a robotic lid mounting arm. Said robotic lid mounting arm being configured to grip a lid from within said culture dish compartment and to move said lid and arrange said lid on top of a culture dish or of a well of a culture dish being accommodated within said culture dish compartment. This is brought about by pivotally arranging a lid mounting arm on a base 88 at one end and at the opposite end providing a working end 90 which by means of a motor unit 92 is being able to be moved independently in three dimensions. The working end 90 comprises a gripping pad 94 which is adapted to be able to grip a lid arranged within the culture dish compartment and which is adapted to place the lid on a culture dish arranged within that culture dish compartment, or on a culture well thereon.

The lid may be in the form of a thin sheet of aluminum or another metal which by use of electromagnetic radiation via induction is being sealed to the culture dish.

In the embodiment shown in 6, the manipulation unit 18 in the form of a robotic lid mounting arm 86 also functions as a manipulation unit for gripping a culture dish and to move it between said culture dish compartment and said cryogenic area of said apparatus.

Figure 7:
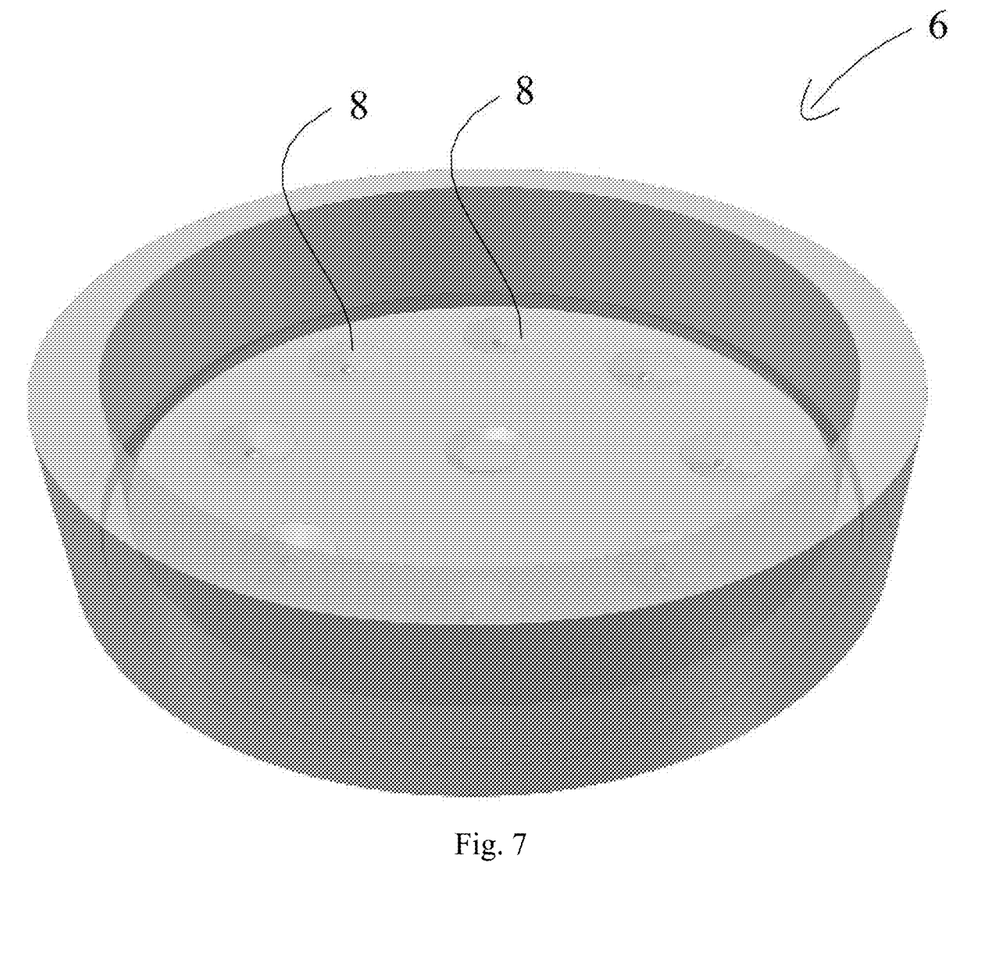
FIG. 7 illustrates in a perspective view one embodiment a culture dish to be used with the apparatus of the present invention.

FIG. 7 illustrates a culture dish 6 to be used with the apparatus illustrated in FIG. 1. The culture dish comprises 8 culture wells for accommodating a viable biological material.

Figure 8A:
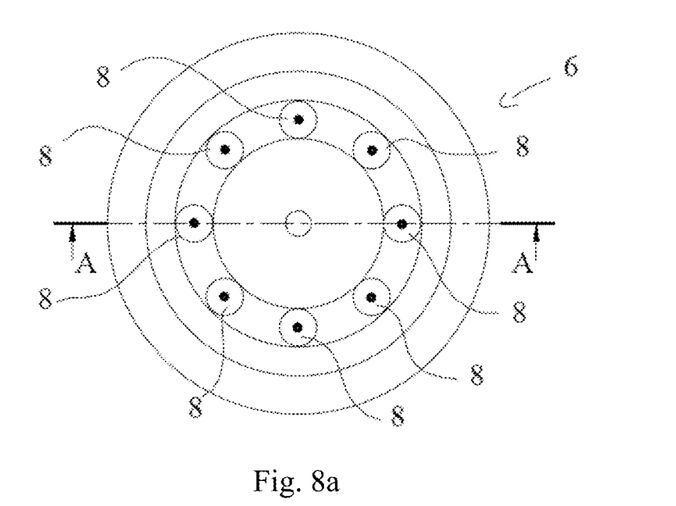
FIGS. 8a, 8b and 8c illustrate in various views the culture dish of FIG. 7.
Figure 8B:
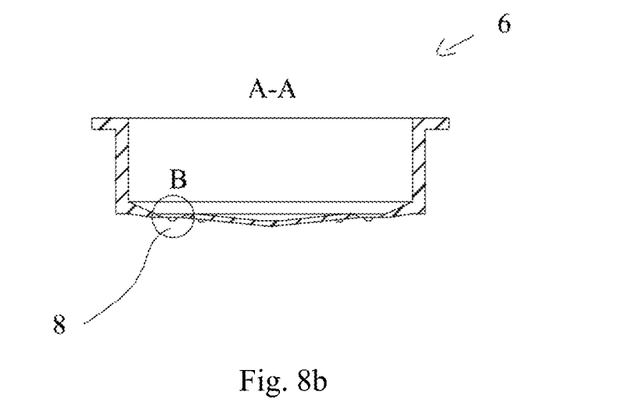
Figure 8C:
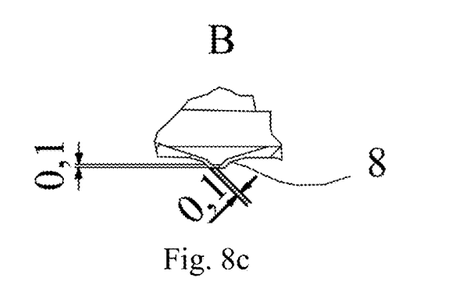

FIGS. 8a, 8b and 8c illustrate in various views the culture dish 6 of FIG. 7. In 8c it can be seen the material below the bottom of the culture wells and the wall of the culture wells is having a thickness of only 0.1 mm. Such a thin bottom below the culture wells provides in an optimum way for instant freezing when the culture dish, or at least the bottom thereof is being exposed to cryogenic conditions.

The culture dish is being manufactured in a transparent material, such as plastic.

LIST OF REFERENCE NUMERALS

2 Housing
4 Culture dish compartment
6 Culture dish
8 Culture well of culture dish
10 Image capturing device
12 Cryogenic means
14 Cryogenic area
16 Operational area
18 Manipulation unit
20 Gripping arm
22 Movement means
24 Control system
26 Lid of apparatus
28 Shelf of culture dish compartment
30 Moving means
32 Pipette pump
34 Pipette stand
36 Container for incubation liquids and/or cryoprotectants
38 Transparent shelf
40 Container for storing liquid gas
42 Input means for setting operational protocols
44 Display for displaying mode/progress of operation
46 Lid holding means
48 Material having a relative high heat conducting capacity
50 Through-going hole
52 Outer periphery of culture dish
54 Inner periphery of culture dish
56 Lid of culture dish
58 Robotic pipetting arm
60 Base of manipulation unit
62 Working end of robotic pipetting arm
64 Pipetting means
66 Pipette
68 Motor unit
70 Stand for pitting pump
72 First bracket of stand for pitting pump
74 Second bracket of stand for pitting pump
76 Plastic syringe
78 Cylinder part of plastic syringe
80 Piston part of plastic syringe
82 Motor unit
84 Passage end of syringe
86 Robotic dish sealing arm, robotic lid mounting arm
88 Base of lid mounting robotic arm
90 Working end of lid mounting robotic arm
92 Motor unit
94 Gripping pad of lid mounting robotic arm
100 Apparatus
200 System
X Longitudinal direction
Y Transversal direction

The invention claimed is:

1. An apparatus (100) for the combined incubation, vitrification and cryopreservation of a viable biological material;

said apparatus comprises:
a housing (2) having an extension in a longitudinal direction (X) and an extension in a transversal direction (Y); said housing comprising:
one or more culture dish compartments (4), each being adapted to accommodate one or more culture dishes (6) comprising a biological material, each said culture dish comprises one or more culture wells (8) for accommodating said biological material;
wherein one or more of said one or more culture dish compartments is being provided with a transparent wall;
wherein said apparatus comprises one or more image capturing devices (10) adapted to capture images of one or more of said biological material accommodated in said one or more culture dishes, while said biological material is being accommodated in its respective culture dish compartment;
wherein said apparatus comprises cryogenic means (12) for cooling at cryogenic temperatures of a biological material, said cryogenic means being arranged in a cryogenic area (14) at a different location relative to said one or more culture dish compartments (4);
wherein said one or more culture dish compartments and said cryogenic area together defines an operational area (16);
wherein said apparatus comprises one or more manipulation units (18), said one or more manipulation units each comprises one or more robotic arms (20), said one or more robotic arms being configured to grip and move elements and/or chemical/biological material within said operational area, wherein said one or more robotic arms being configured to grip a lid from within said culture dish compartment and to move said lid and arrange said lid on top of one culture dish being accommodated in said culture dish compartment, thereby providing automatic sealing of said culture dish or of one or more wells of said culture dish according to a predetermined protocol and prior to cryopreservation;
wherein said apparatus comprises a device that is configured to move said image capturing device relative to said culture dishes along said one or more individual culture dish compartments, at positions outside said transparent wall(s), relative to the interior of said individual culture dish compartment;

wherein said apparatus is configured for fully automated operation during vitrification and cryopreservation;

wherein said cryogenic means comprises a container comprising a liquid gas;

wherein said one or more image capturing devices (10) is configured to focus in a horizontal direction; and wherein movement of said one or more image capturing devices (10) occurs in front of/behind said one or more culture dish compartments, while still being present within the housing of the apparatus.

2. An apparatus (100) according to claim 1, wherein said apparatus comprises two or more individual culture dish compartments.

3. An apparatus (100) according to claim 2, furthermore comprising temperature regulating means for individually regulating the temperature in one or more of said individual said culture dish compartments (4).

4. An apparatus (100) according to claim 3, wherein said temperature regulating means comprises at least one of: (1) one or more electric heating elements; and (2) cooling means includes one or more Peltier elements.

5. An apparatus (100) according to claim 2, furthermore comprising gas composition regulator for individually regulating the gas composition in one or more of said individual culture dish compartments.

6. An apparatus (100) according to claim 2, wherein said apparatus comprises an image capturing device (10) in respect of each individual culture dish compartment.

7. An apparatus (100) according to claim 6, further comprising movement means (10) that is configured in such a way that said image capturing device is adapted for being moveable relative to said one or more culture dishes, thereby allowing capturing of images of each biological material accommodated in said one or more culture dishes.

8. An apparatus (100) according to claim 6, wherein said culture dish compartment comprises a shelf (28) for accommodation of a culture dish and a movement means (30) is configured in a way allowing said shelf to be moved relative to said image capturing device (10), thereby allowing capturing of images of each biological material accommodated in said respective culture dish.

9. An apparatus (100) according to claim 2, wherein at least one culture dish compartment of said two or more culture dish compartments comprises a pipette pump (32), said pipette pump being configured for pipetting fluids to and from said culture well of said culture dish.

10. An apparatus (100) according to claim 2, wherein at least one culture dish compartment of said two or more culture dish compartments comprises one or more pipette stands (34) comprising one or more pipettes.

11. An apparatus (100) according to claim 2, wherein at least one culture dish compartment of said two or more culture dish compartments comprises one or more containers (36) for storing at least one of incubation liquids and cryoprotectants.

12. An apparatus (100) according to claim 11, wherein said one or more containers comprising a sealing syringe end cap.

13. An apparatus (100) according to claim 2, wherein said container for storing the liquid gas is separated from said two or more culture dish compartments.

14. An apparatus (100) according to claim 6, wherein said apparatus comprising an image processing unit for processing images captured by said image capturing device (10).

15. An apparatus (100) according to claim 6, wherein said image capturing device (10) comprises a microscope for capturing close-up images of said biological material.

16. An apparatus (100) according to claim 2, wherein one of said one or more manipulation units (18) comprises a robotic dish sealing arm (86), wherein said robotic dish sealing arm is being configured for sealing one or more culture dishes (6), or for sealing a well (8) of one culture dish, being accommodated within said culture dish compartment (4).

17. An apparatus (100) according to claim 2, wherein one of said one or more manipulation units (18) comprises a robotic pipetting arm (58), said robotic pipetting arm comprises a pipette (66) and wherein said robotic pipetting arm being configured to move said pipette within said culture dish compartment, (4) so as to allow withdrawing and/or adding liquids and/or suspensions to or from one or more culture wells (8) of one culture dish (6) being accommodated within said culture dish compartment.

18. An apparatus (100) according to claim 2, wherein one of said one or more manipulation units (18) comprises a robotic culture dish moving arm, wherein said robotic culture dish moving arm being configured to grip a culture dish and to move it between said culture dish compartment and said cryogenic area of said apparatus.

19. An apparatus (100) for the combined incubation, vitrification and cryopreservation of a viable biological material;

said apparatus comprises:

a housing (2) having an extension in a longitudinal direction (X) and an extension in a transversal direction (Y); said housing comprising:

one or more culture dish compartments (4), each being adapted to accommodate one or more culture dishes (6) comprising a biological material, each said culture dish comprises one or more culture wells (8) for accommodating said biological material;

wherein one or more of said one or more culture dish compartments is being provided with a transparent wall;

wherein said apparatus comprises one or more image capturing devices (10) adapted to capture images of one or more of said biological material accommodated in said one or more culture dishes, while said biological material is being accommodated in its respective culture dish compartment;

wherein said apparatus comprises cryogenic means (12) for cooling at cryogenic temperatures of a biological material, said cryogenic means being arranged in a cryogenic area (14) at a different location relative to said one or more culture dish compartments (4);

wherein said one or more culture dish compartments and said cryogenic area together defines an operational area (16);

wherein said apparatus comprises one or more manipulation units (18), said one or more manipulation units each comprises one or more robotic arms (20), said one or more robotic arms being configured to grip and move elements and/or chemical/biological material within said operational area, wherein said one or more robotic arms being configured to grip a lid from within said culture dish compartment and to move said lid and arrange said lid on top of one culture dish being accommodated in said culture dish compartment, thereby providing automatic sealing of said culture dish or of one or more wells of said culture dish according to a predetermined protocol and prior to cryopreservation;

wherein said apparatus is configured to move said image capturing device relative to said culture dishes along said one or more individual culture dish compartments, at positions outside said transparent wall(s), relative to the interior of said individual culture dish compartment;

wherein said apparatus is configured for fully automated operation during vitrification and cryopreservation;

wherein said cryogenic means comprises a container comprising a liquid gas;

wherein said one or more image capturing devices (10) is configured to focus in a horizontal direction; and wherein movement of said one or more image capturing devices (10) occurs in front of/behind said one or more culture dish compartments, while still being present within the housing of the apparatus.

* * * * *